(12) United States Patent
Stenman et al.

(10) Patent No.: US 7,838,228 B2
(45) Date of Patent: Nov. 23, 2010

(54) METHOD OF QUANTITATIVE AND/OR COMPARATIVE MEASUREMENT OF MRNA EXPRESSION LEVELS IN SMALL BIOLOGICAL SAMPLES

(75) Inventors: Jakob Stenman, Espoo (FI); Annukka Paju, Vantaa (FI); Oso Rissanen, Turku (FI); Arto Orpana, Helsinki (FI)

(73) Assignee: Expression Analytics Oy, Espoo (FI)

( * ) Notice: Subject to any disclaimer, the term of this patent is extended or adjusted under 35 U.S.C. 154(b) by 258 days.

(21) Appl. No.: 11/596,543

(22) PCT Filed: May 25, 2005

(86) PCT No.: PCT/FI2005/050176

§ 371 (c)(1),
(2), (4) Date: Dec. 13, 2006

(87) PCT Pub. No.: WO2005/116248

PCT Pub. Date: Dec. 8, 2005

(65) Prior Publication Data

US 2008/0286769 A1    Nov. 20, 2008

(30) Foreign Application Priority Data

May 26, 2004    (FI) ................................ 20040723

(51) Int. Cl.
*C12Q 1/68*    (2006.01)
*C12P 19/34*    (2006.01)

(52) U.S. Cl. .......................................... 435/6; 435/91.2
(58) Field of Classification Search ........................ None
See application file for complete search history.

(56) References Cited

U.S. PATENT DOCUMENTS

| 5,741,676 | A  | * | 4/1998 | Fuller .................... 435/91.1 |
| 6,280,931 | B1 |   | 8/2001 | Sakamoto et al. |
| 6,618,679 | B2 | * | 9/2003 | Loehrlein et al. ............. 702/20 |
| 2003/0022175 | A1 |   | 1/2003 | Terng et al. |
| 2003/0235884 | A1 |   | 12/2003 | Cummings et al. |
| 2004/0091857 | A1 |   | 5/2004 | Nallur et al. |
| 2004/0091921 | A1 |   | 5/2004 | Uematsu et al. |

FOREIGN PATENT DOCUMENTS

| EP | 0 825 265 A1 | 2/1998 |
| EP | 1 279 743 A2 | 1/2003 |
| JP | 2001-78768 A | 3/2001 |
| WO | WO-98/35058 A2 | 8/1998 |
| WO | WO-01/02603 A1 | 1/2001 |
| WO | WO-01/20041 A1 | 3/2001 |
| WO | WO-/2005/110596 A2 | 11/2005 |

OTHER PUBLICATIONS

Lyon et al. Quantification of HER2/neu gene amplification by competitive PCR using fluorescent melting curve analysis. Clinical Chem. (2001) vol. 47, No. 5, pp. 844-851.*
Joo et al., "Differential amplifying RT-PCR: a novel RT-PCR method to differentiate mRNA from its DNA lacking intron," Journal of Virological Methods, vol. 100, pp. 71-81, (2002). XP-002348045.
Waksman et al., "The Central Cannabinoid Receptor (CB1) Mediates Inhibition of Nitric Oxide Production by Rat Microglial Cells", Journal of Pharmacology and Experimental Therapeutics, vol. 288, No. 3, 1999, p. 1357-1366.
Yotsuyanagi et al., "Regulation of Fas gene expression in HeLa cells as determined by modified RT-PCR", Cell. Mol. Life Sci., vol. 54, 1998, p. 186-190.
Sun et al., "Quantifying porphobilinogen deaminase mRNA in microdissected nephron segments by a modified RT-PCR", Kidney International, vol. 61, 2002, p. 336-341.
M. E. Zenilman et al., Analytical Biochemistry, 224, No. 1, pp. 339-346, Jan. 1, 1995.
J. Stenman et al., Nature Biotechnology, vol. 17, pp. 720-722, Jul. 1999.
J. Stenman et al., BioTechniques, vol. 34, No. 1, pp. 172-177 (2003).
L Stryer, Biochemistry, 4th ed. Second printing 1995, KP, Part I: Molecular design of life, pp. 139-140.
U.S. Appl. No. 60/569,822, filed May 10, 2004.

* cited by examiner

*Primary Examiner*—Kenneth R. Horlick
*Assistant Examiner*—David C Thomas
(74) *Attorney, Agent, or Firm*—Birch, Stewart, Kolasch & Birch, LLP

(57) ABSTRACT

The present invention provides a method for quantitative and/or comparative assessment of the relative amounts of mRNA transcripts present in a cell or tissue sample. In the method reverse transcription of the mRNA contained in the sample is first carried out using sequence-modifying primers for one or several genes in the same reaction to obtain a pool of sequence-modified cDNA molecules. After completion of the reverse transcription redundant sequence-modifying primers are removed or inactivated. This step is followed by a step of co-amplifying the sequence-modified cDNA templates with a reference DNA template in individual gene-specific amplification reactions. By quantitatively measuring the amounts and determining the relative levels of the amplification products derived from sequence-modified cDNA and reference DNA templates, a gene-specific cDNA over DNA ratio is obtained in each of the individual amplification reactions. Finally, by combining the ratios obtained, a sample-specific profile can be generated, which reflects the relative amounts of mRNA transcripts originally present in the sample.

24 Claims, 7 Drawing Sheets

SEQUENCE-MODIFYING REVERSE TRANSCRIPTION PRIMER

FIGURE 2  Competitive cDNA / DNA gene expression analysis

METHOD OF QUANTITATIVE AND/OR COMPARATIVE MEASUREMENT OF MRNA EXPRESSION LEVELS IN SMALL BIOLOGICAL SAMPLES

FIELD OF THE INVENTION

The present invention relates to the diagnosis of pathological and physiological conditions in humans and to the monitoring of treatment as well as follow-up of such conditions. The invention also relates to the characterization of cell- or tissue-specific changes in gene-expression patterns and pathways in various conditions. The described technique enables comparative and/or quantitative measurement of mRNA transcripts contained in small cell or tissue samples.

BACKGROUND OF THE INVENTION

The development of technologies related to biological sciences has led to a rapid increase in available genetic information. The completion of the sequencing of the human genome and the Human Genome Project's policy of instant data accessibility has created a fundament for studying gene-expression in physiological and pathological conditions. Techniques such as gene expression microarrays, differential display polymerase chain reaction (DD-PCR) and quantitative reverse transcriptase polymerase chain reaction (qRT-PCR) together with statistical clustering algorithms have provided tools for characterization of gene-expression patterns and pathways. This has led to the defining of new subcategories of known diseases, based on gene expression profiles, with different prognoses and potentially different responses to specific drugs and other treatment modalities.

DNA microarray technology has been the main contributor to the rapidly accumulating gene expression data. Using this technology, gene expression-based classifications have been developed for several malignant diseases. At present, gene expression microarray technology, however, has major technical shortcomings as a diagnostic method in a clinical laboratory as it is fairly insensitive and the quantitative precision is only moderate.

Gene expression analysis in a clinical setting is subjected to specific technical challenges due to the characteristics of the different types of clinical samples. Solid tissue samples such as histological paraffin-embedded or frozen tissue specimen usually contain a heterogeneous mixture of different cell types. Measurement of gene expression in a specific cell or tissue type within the sample requires isolation of cells or islets of cells from microscopic sections, e.g. by microdissection, or scoring of the relative amounts of different cell types present in sections cut from the sample. In needle biopsies and cytological samples the amount of sampled cells is usually small and the exact amount of cells is unknown. In blood samples the proportion of target cells is in many cases small and enrichment of specific cell types in the samples is required. Messenger RNA (mRNA) recovery from these types of samples is often limited, thus increasing the sensitivity requirements on the techniques used for gene expression analysis. In addition, sample-to-sample variations in mRNA degradation and recovery occur during sample preparation and storage as well as during nucleic acid purification. In order to obtain comparable results from tissue samples obtained in vivo, normalization for sample-to-sample variations in mRNA levels and integrity is required.

qRT-PCR has been widely used to validate results on gene expression levels that have been obtained using gene expression microarrays. The sensitivity of qRT-PCR is sufficient for quantitative measurement of gene expression in samples containing minimal amounts of cells or even single cells. Because of the logarithmic nature of the amplification of nucleic acids during PCR, this technique is sensitive to tube-to-tube variations due to small differences in reaction efficiencies. To overcome this problem, RNA or DNA internal control templates can be added to the samples to monitor the reaction efficiencies in individual reactions. Sample-to-sample variations in mRNA levels and integrity is typically controlled by normalizing mRNA expression levels of specific genes of interest against the expression levels of housekeeping genes or the amount of total RNA or ribosomal RNA (rRNA) in the sample, or by comparative quantification of mRNA from multiple genes in the same sample.

A method of modifying the size of the cDNA template during reverse transcription in order to discriminate it from genomic DNA has been described by Joo et al. (in Journal of Virological Methods 100 (2002) pages 71-81, and in patent application KR2002089746 A). In this technique a size-modifying-anchor primer is used in the reverse transcription reaction to insert a modified primer-binding site into the generated cDNA. This technique relies on the assumption that genomic DNA remains double-stranded when reverse transcription is performed under non-denaturing conditions, and thus cannot function as a template for reverse transcription. In the amplification step the cDNA and genomic DNA templates from the same gene are amplified using one common upstream primer and separate down-stream primers. The generated cDNA- and genomic DNA-derived amplicons differ in length to allow separate detection and quantification. Generally, RT-PCR techniques require amplification of a sequence that traverses at least one exon-exon boundary in order to enable separation of the cDNA- and genomic DNA-derived amplification products. The technique described by Joo et al. enables differentiation of cDNA from its corresponding genomic DNA within the boundaries of a single exon after RT-PCR amplification. It also allows comparison of relative levels of gene-specific mRNA and DNA.

The present invention provides a method for quantitative and/or comparative assessment of the relative amounts of mRNA transcripts present in a cell or tissue sample. In this method sequence-modified cDNA templates are competitively co-amplified with a reference DNA template using the very same primers. This enables using genomic DNA contained in, or added to the sample, as a universal reference template to normalize for tube-to-tube variations in amplification efficiencies between separate gene-specific amplification reactions. By quantitatively measuring the amounts and determining the relative levels of the amplification products derived from sequence-modified cDNA and reference DNA templates, a gene-specific cDNA over DNA ratio is obtained in each individual amplification reaction. By combining the cDNA over DNA ratios for each of the analyzed genes, a sample-specific gene-expression profile is generated, that reflects the relative amounts of mRNA transcripts originally present in the sample.

In the present invention, sequence-modified cDNA and reference DNA templates are co-amplified with the very same primers in the same reaction vessels. Thus, the relative levels of the cDNA and reference template derived amplification products remain constant even when amplification reactions are run to the plateau phase. This enables optimization of the sensitivity of the assay for samples containing only minimal amounts of mRNA transcripts.

SUMMARY OF THE INVENTION

The present invention provides a method, in which reverse transcription is carried out using sequence-modifying primers for one or several genes in the same reaction to obtain a pool of sequence-modified cDNA molecules. The cDNA molecules are modified at one or several nucleotide positions without altering the primer-binding sites used in subsequent amplification reactions. After completion of the reverse transcription reaction redundant sequence-modifying primers are removed or inactivated, i.e. prevented from participating in subsequent amplification reactions. Individual amplification reactions are carried out for each of the analyzed genes, so that in each of the reactions sequence-modified cDNA and reference DNA templates are co-amplified in a competitive manner, using the same gene-specific primers. The reference DNA template comprises genomic DNA contained in the analyzed sample or added to the sample prior to amplification. It can also comprise synthetic or cloned DNA. The sequence modifications generated during reverse transcription are incorporated in the cDNA-derived amplification products and used for separate detection and determination of the ratio of the cDNA and reference DNA template-derived amplification products in each of the individual amplification reactions. The gene-specific cDNA over DNA ratios determined in the individual amplification reactions are combined to generate a sample-specific profile of said ratios that reflects the relative amounts of mRNA transcripts originally present in the sample.

Consequently, the primary object of the present invention is a method for quantitative and/or comparative assessment of the relative amounts of mRNA transcripts present in a cell or tissue sample, which method is characterized by the steps (a) to (e) as defined in the appended claim 1. The different ways for implementing the method of the invention are described below.

Figure 1:
FIG. 1
Figure 2:
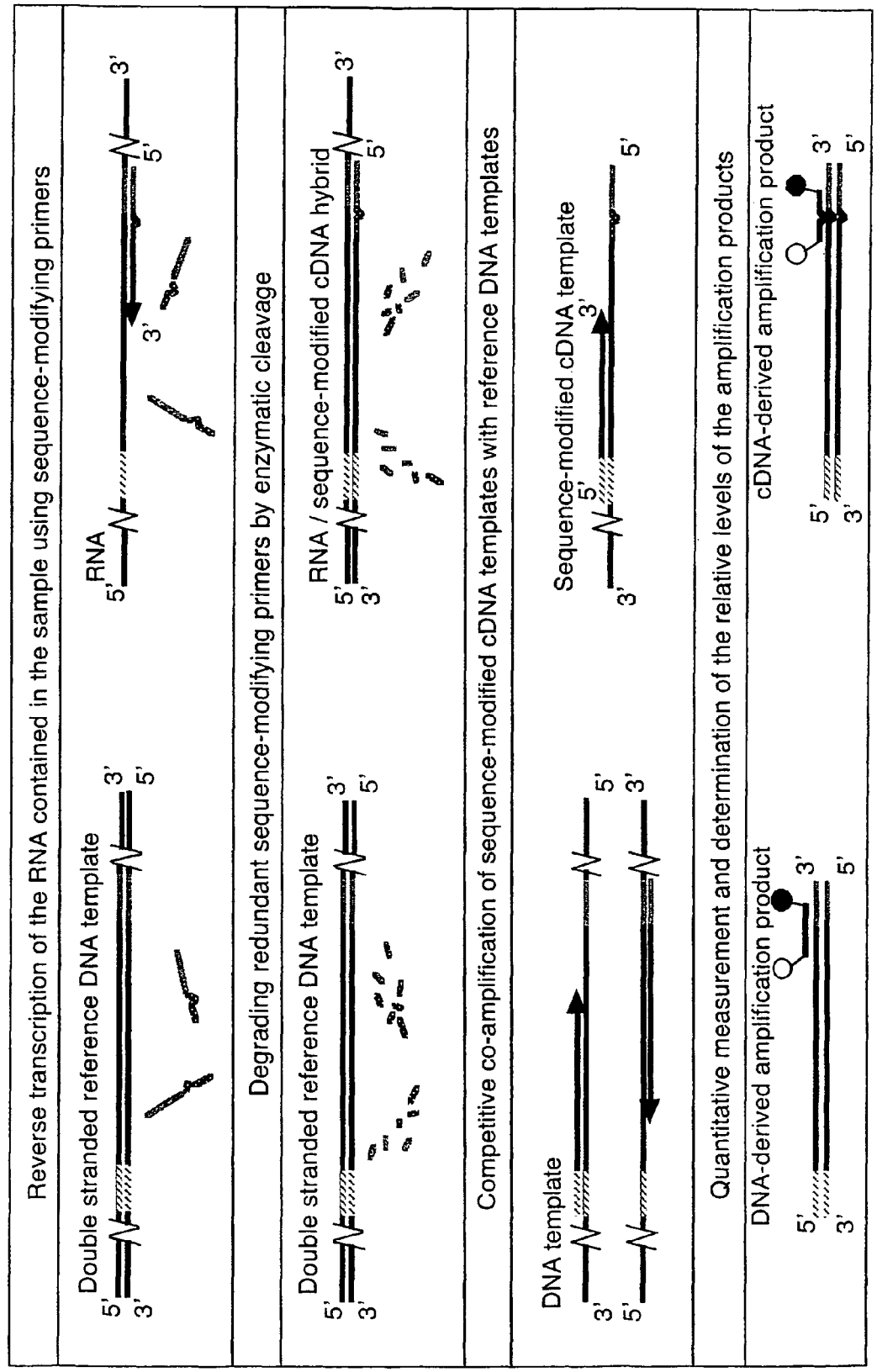

Schematic drawing showing the functional segments of the sequence-modifying primers.

FIG. 2

Schematic drawing of the principle of the present invention. The reference DNA template can be included in the reverse transcription step as shown (top panel), or it can be added prior to the amplification step. In the detection step (bottom panel) a dual-labeled hybridization probe is shown for illustrative purposes. The present invention is, however, not dependent on any specific detection technique, but any method enabling separate quantitative detection of the cDNA and reference DNA template-derived amplification products can be used.

FIG. 3

Measuring range of the assay for quantifying the relative levels of cDNA and reference DNA templates. 10-fold dilutions of cDNA, reverse transcribed from $10^9$ copies of trypsinogen-1 cRNA and $10^3$ copies of cloned trypsinogen DNA (upper panels) or genomic DNA from 500 cells (lower panels) were co-amplified in nested PCR reactions. The amplification products of the sequence-modified cDNA and genomic DNA were detected and quantified by solid-phase minisequencing. The measuring range of the assay more than two orders of magnitude (shown in black in the panels on the right-hand side). The theoretical cDNA template copy number is based on the assumption that the efficiency of the reverse transcription reaction was 100%.

FIG. 4

Capacity of the minisequencing assay to discriminate between templates differing at single nucleotide positions. The PCR products derived from trypsinogen-1 cDNA (top panel), cloned trypsinogen-1 DNA (middle panel) and genomic DNA from tumor cells (bottom panel) were minisequenced with four different $^3$H-labelled nucleotides (dCTP, dGTP, dATP, and dTTP).

FIG. 5

Reproducibility of the assay in analyzing an expression profile of genes in cultured cells. Expression profile of MMP-2, MMP-9, uPA, uPAR, and p53 genes in cultured COLO 205 cells as analyzed in five separate experiments during a two months period. The sum of the cDNA to genomic DNA ratios of the individual genes in the each separate experiment is adjusted to 100.

FIG. 6

Reproducibility of the assay in analyzing an expression profile of genes in cultured cells. Expression profile of MMP-2, MMP-9, uPA, uPAR, and p53 genes in cultured COLO 205 cells as analyzed in five separate experiments during a two months period. The results represent the mean values ±1 standard errors from the five separate experiments. The sum of the cDNA to genomic DNA ratios of the individual genes in the each separate experiment is adjusted to 100.

FIG. 7

Measuring range of the assay for quantifying the relative levels of cDNA and reference DNA templates. 10-fold dilutions of cDNA, reverse transcribed from 109 copies of trypsinogen-2 (upper panel) or matrix-metalloproteinase-2 (MMP-2) (lower panel) cRNA and 20 ng human genomic DNA were co-amplified in a PCR reaction on a LightCycler instrument. The amplification products of the sequence modified cDNA and genomic DNA templates were quantified by melting curve analysis on a LightCycler instrument. The measuring range of the assay was more than two orders of magnitude (shown in black in the panels on the right-hand side). The theoretical cDNA template copy number is based on the assumption that the efficiency of the reverse transcription reaction was 100%.

DETAILED DESCRIPTION OF THE INVENTION

Samples and Reference Templates

The present invention provides a method for quantitative and/or comparative assessment of the relative amounts of mRNA transcripts present in a cell or tissue sample. The sample comprises a cell or tissue lysate or homogenate. The reference DNA template comprises genomic DNA contained in the sample or isolated from a separate source, or cloned or synthesized DNA oligo- or polynucleotides. When genomic DNA contained in the sample is used as a reference DNA template, RNA and genomic DNA can be isolated from the sample prior to reverse transcription. When genomic DNA contained in the sample is not used as a reference DNA template, RNA is isolated from the sample prior to reverse transcription. The reference DNA template is present in or added to each of the samples prior to amplification. The reference DNA template can be present in the sample during reverse transcription provided that it is double stranded. When the reference DNA template is other than genomic DNA contained in the sample, it is preferably added in equal amounts to each of the samples after reverse transcription but prior to amplification.

Modification of the cDNA Sequence During Reverse Transcription

Reverse transcription of the mRNA contained in the sample is carried out using sequence-modifying primers for one or several genes in the same reaction to obtain a pool of sequence-modified cDNA molecules. When a reference DNA template is present in the reaction mixture during reverse transcription, the reverse transcription reaction is carried out under non-denaturing conditions where DNA contained in the sample remains mainly double-stranded and does not function as a template for cDNA synthesis.

The sequence-modifying primers (FIG. 1) comprise three functional segments; a 5'-terminal segment comprising a nucleotide sequence, which is complementary to the mRNA sequence as well as the sense strand DNA sequence of a specific gene, and contains the complementary nucleotide sequence of the binding sites for the downstream primers used in subsequent amplification reactions, a central segment consisting of a nucleotide sequence comprising one or multiple nucleotides, which are non-complementary to the mRNA sequence as well as the sense strand DNA sequence of said gene, and a 3'-terminal segment comprising a nucleotide sequence, which is complementary to the mRNA sequence as well as the sense strand DNA sequence of said gene.

The generated cDNA thus contains a sequence modification comprising one or multiple nucleotide substitutions, insertions or deletions as compared with the antisense strand of the corresponding genomic DNA nucleotide sequence. The nucleotide sequence modifications are located in such a manner that they will be incorporated in the amplification products but do not affect the nucleotide sequence of the primer-binding sites used in the sub-sequent amplification reactions. This enables co-amplification of the modified cDNA templates with a reference DNA template comprising genomic DNA, using the very same primers.

Removal or Inactivation of Redundant Primers after Reverse Transcription

After completion of the reverse transcription, it is essential to prevent redundant sequence-modifying primers from functioning as primers in the subsequent gene-specific amplification reactions. Any intact sequence-modifying primers transferred from the reverse transcription step to the amplification reactions could prime the amplification of the reference DNA template, causing modification of the nucleotide sequence in part of the reference DNA template-derived amplification product. Such modifications would be identical to the sequence-modification generated in the cDNA transcript during reverse transcription, rendering part of the reference DNA template-derived amplification products identical and thus indistinguishable from the amplification product derived from the sequence-modified cDNA template. Thus, quantification of the relative amounts of cDNA- and DNA-derived amplification products would not reflect the true amounts of sequence-modified cDNA and reference DNA templates present in the sample prior to amplification.

Redundant sequence-modifying primers can be removed or inactivated, i.e. prevented from functioning as primers in subsequent gene-specific amplification reactions by, for instance, enzymatic degradation using single-stranded DNA-specific exonuclease. As a result, single-stranded oligonucleotide primers are degraded but double-stranded mRNA-cDNA hybrids and reference DNA contained in the sample are left intact. Alternatively, redundant sequence-modifying primers can be physically removed from the sample by filtration or other means prior to the amplification step.

Any sequence-modifying primers transferred from the reverse transcription reactions to the gene-specific amplification reactions can also be prevented from functioning as primers by hybridization to blocking oligonucleotides or other agents that bind specifically to the 3'-terminal and/or central functional segments of the sequence-modifying primers.

Co-Amplification of the Sequence-Modified cDNA and Reference DNA Templates

Following reverse transcription and removal or inactivation of redundant sequence-modifying primers, aliquots of the reaction mixture are transferred to separate amplification reactions. Individual amplification reactions are carried out in physically separate vessels for each of the analyzed genes, so that in each of the reactions sequence-modified cDNA templates are co-amplified with the same reference DNA template, using gene-specific primers to generate measurable amounts of amplification products. The cDNA and reference DNA templates in an individual amplification reaction are co-amplified in a competitive manner, using the very same primers. Amplification can be performed in a single reaction or in two consecutive reactions using nested primers. The binding sites of the amplification primers are preferably located on the same exon in order to generate cDNA and DNA derived amplification products of equal or close-to-equal length. The binding sites of the amplification primers are located in such a manner that the sequence modification generated in the cDNA template will be incorporated in the amplification product. Co-amplification of the sequence-modified cDNA and reference DNA templates in the same reaction and with the very same primers results in close-to-equal amplification efficiencies for the two templates, even when amplification reactions are run to the plateau phase. As a result, the relative levels of amplification products deriving from sequence-modified cDNA templates and reference DNA templates in an individual gene-specific amplification reaction reflect the relative amounts of said templates originally present in the amplification reaction prior to amplification. Amplification can be carried out using polymerase chain reaction, ligase chain reaction, transcription-mediated amplification or any other enzymatic reaction that enables amplification of two similar templates in the same reaction in a competitive manner so that the sequence-modifications generated in the cDNA templates during reverse transcription are incorporated in the cDNA-derived amplification products.

Detection and Quantitative Measurement of the Amplification Products Deriving from Sequence-Modified cDNA and Reference DNA Templates In the present invention a modification in the nucleotide sequence of the cDNA molecules is generated during reverse transcription. These sequence modifications are incorporated in the cDNA-derived amplification products and used to distinguish the cDNA-derived amplification products from the reference DNA template-derived amplification products present in the same amplification reaction.

Quantitative measurement of the amplification products can be carried out during amplification (real-time or kinetic detection) using sequence-specific dual-labeled hydrolysis probes, fluorescence resonance energy-transfer probes, MOLECULAR BEACON® probes or any other technology that allows separate quantitative detection of the cDNA and reference DNA template-derived amplification products. Quantitative measurement of the amplification products can also be carried out after completion of the amplification reaction (endpoint detection) using Minisequencing (single nucleotide primer extension), cyclic minisequencing, PYROSEQUENCING®, allele-specific primer extension, melting curve analysis, sequence-specific hybridization probes, mass spectrometry, or any other technology that allows separate quantitative detection of the cDNA and reference DNA template-derived amplification products.

Interpretation of Results

Co-amplification of the sequence-modified cDNA and reference DNA templates in the same reaction with the very same primers results in close-to-equal amplification efficiency for the two templates even when amplification reactions are run to the plateau phase. As a result, the relative levels of amplification products deriving from sequence-modified cDNA and reference DNA templates in an individual gene-specific amplification reaction remain constant throughout amplification, and reflect the relative amounts of said templates originally present in the sample prior to amplification. By quantitatively measuring the amounts and determining the relative levels of the amplification products derived from sequence-modified cDNA and reference DNA templates, a gene-specific cDNA over DNA ratio is obtained in each of the individual amplification reactions. A sample-specific profile is generated by combining the gene-specific cDNA over DNA ratios determined for each of the analyzed genes in the individual amplification reactions. The cDNA over DNA ratios in the sample-specific profiles reflect the relative amounts of mRNA transcripts originally present in the sample and can be used for comparative analysis of variations in the mRNA levels of the analyzed genes between separate samples. If genomic DNA contained in the sample is used as a reference DNA template, potential variations in the copy number of the analyzed genes in the genome of the cells in the sample need to be taken into consideration.

Definitions

The term "sequence-modifying primer" means an oligonucleotide primer that is used in the reverse transcription reaction in order to generate a nucleotide sequence modification in the cDNA sequence as compared with the wild type nucleotide sequence of a specific target gene. Gene-specific sequence-modifying primers for several different genes can be used in the same reverse transcription reaction to generate a pool of sequence-modified cDNA molecules.

The term "co-amplification" means simultaneous amplification of two or multiple cDNA and/or DNA templates with differing nucleotide sequences within the generated amplification products. A prerequisite for co-amplification as the term is used in this patent application is that templates have identical nucleotide sequences at the primer-binding sites used in the amplification reaction and that amplification of the said templates is carried out in a competitive manner with the same primers and other reagents, in the same reaction vessel.

The term "reference DNA template" means a DNA template that is included in each amplification reaction and serves to normalize for tube-to-tube variations in amplification efficiency. Reference DNA templates comprise genomic DNA contained in or added to the sample, or a pool of gene-specific templates such as cloned or synthesized DNA oligo- or polynucleotides for each of the analyzed genes. The sequence-modified cDNA and reference DNA templates in an individual amplification reaction are co-amplified in a competitive manner, using the same primers. Gene-specific synthetic or cloned reference DNA templates can be concatenated by ligation or other means to form a single polynucleotide that functions as a universal reference DNA template for several genes.

The term "removal or inactivation of redundant sequence-modifying primers" means for the purposes of this invention any action taken to prevent redundant sequence-modifying primers from functioning as primers in the gene-specific amplification reactions subsequent to the reverse transcription reaction. Such actions may be, for instance, enzymatic degradation of the primers, physical separation of the primers from the sample, or hybridization of the primers to any appropriate blocking agent.

The present invention is described in more detail in the following examples, which are presented for illustrative purposes only and should not be considered to limit the scope of the invention. Those skilled in the art can easily apply the principles of the invention for different applications.

EXAMPLE 1

Experimental Design and Proving the Principle

The experiment was conducted in order to define the measuring range of the assay over a range of cDNA/DNA ratios. In this experiment the principle of the present invention was proven by analyzing a dilution series of sequence-modified cDNA reverse-transcribed from the cRNA of a single gene in relation to the reference DNA template which was A) a fixed amount of cloned DNA copies from the same gene or B) genomic DNA.

Preparative Steps

Trypsinogen-1 DNA clone containing bases 46-714 of trypsinogen-1 cDNA sequence was generated from pancreatic cDNA (Clontech) by PCR. The sequence of the DNA clone was checked by sequencing from both ends on an ABI Prism 310 genetic analyzer, (Applied Biosystems) using the ABI Prism dye terminator cycle sequencing core kit and AmpliTaq DNA polymerase. Trypsinogen-1 cRNA was generated by in vitro transcription using trypsinogen-1 DNA clone as a template (Epicentre Technologies), and purified by RNeasy Mini Kit (Qiagen). Tumor cells were grown at 37° C. in a humidified atmosphere with 5% $CO_2$. The cells were maintained in RPMI 1640 medium supplemented with 10% heat-inactivated fetal bovine serum, 2 mM L-glutamine and 100 units/ml penicillin and 100 µg/ml streptomycin. Genomic DNA from these cells was extracted by RNA/DNA Mini Kit (Qiagen).

The Analytical Procedure

Reverse Transcription

Reverse transcription was performed using ThermoScript Rnase H⁻ Reverse Transcriptase (Invitrogen) according to the manufacturer's instructions in a 20-µl reaction volume in cDNA synthesis buffer (50 mM Tris acetate, pH 8.4; 75 mM potassium acetate; 40 mM magnesium acetate), 5 mM DTT, 1 mM dNTP, 20 pmol of sequence-modifying antisense primer to create a single nucleotide C to G substitution in the generated cDNA (5'-CAC ATA GTT GTA GAC CTT GGT GTA GAC TC<u>G</u> AGG C (SEQ ID NO: 1)), 7.5 U of Thermo-Script RT, and $5 \times 10^9$ copies of trypsinogen-1 cRNA. The reaction mixture was incubated at 65° C. for 50 min and at 85° C. for 5 min.

Exonuclease I Treatment

Following reverse transcription, the unbound sequence-modifying reverse transcription primers were cleaved by exonuclease I (New England Biolabs) in a 25-µl reaction volume in 1× restriction buffer (67 mM Glycine-KOH, 6.7 mM $MgCl_2$, 10 mM 2-mercaptoethanol, pH 9.5) and with 20 U of exonuclease I at 37° C. for 60 min and at 80° C. for 20 min. The exonuclease I treated cDNA was serially diluted 10-fold prior to amplification.

Nested Polymerase Chain Reaction

5 µl of each of the dilutions of the reverse transcription product were amplified with A) $10^3$ copies of trypsinogen-1 DNA clone and B) genomic DNA from 500 tumor cells in a 45-µl reaction volume in 1×PCR buffer (10 mM tris-HCl, pH 8.8, 1.5 mM $MgCl_2$, 50 mM KCl, 0.1% Triton X-100; Finnzymes), containing 0.2 mM of each dNTP, 20 pmol of the sense primer (5'-TGA TTC TGG TGG CCC TGT-3' (SEQ ID NO: 2)) and the antisense primer (CAC ATA GTT GTA GAC CTT GGT G (SEQ ID NO: 3)), and 2 U of Dynazyme II DNA polymerase (Finnzymes) by first denaturing the templates for 5 min at 95° C. and then amplifying them for 35 cycles at 95° C. for 1 min and at 55° C. for 1 min. Then, 3 µl of the first amplification product was further amplified in a 75-µl reaction volume using 7.6 pmol of the biotinylated nested sense primer (BIO-5'-CTG GTG GCC CTG TGG TCT-3' (SEQ ID NO: 4)) and 76 pmol of the nested antisense primer (5'-AGA CCT TGG TGT AGA CTC (SEQ ID NO: 5)-3') with the same PCR program as the first PCR. Three controls containing $10^3$ copies of trypsinogen-1 DNA clone, genomic DNA from 500 cells, and sequence modified cDNA reverse transcribed from $10^9$ copies of trypsinogen-1 cRNA, respectively, were included in the experiment. A 15-µl aliquot of the PCR product was separated in 1.5 agarose gel and stained with ethidium bromide in order to exclude non-specific amplification.

Quantitative Detection by Minisequencing

The amplification products of the sequence modified cDNA and reference DNA templates were detected by a modification of a solid-phase minisequencing reaction using $^3$H-labeled nucleotides (Syvänen et al., Genomics (1990) 8:684-692; Ihalainen et al., Biotechniques (1994) 16:938-943; Suomalainen and Syvänen, Methods Mol. Biol. (1998) 86:121-131). Following PCR amplification, 10 µl of the PCR product was captured on a streptavidin-coated scintillating microtitration plate wells (Perkin-Elmer Wallac) with 40 µl of buffer (0.15 M NaCl, 20 mM Na-phosphate pH 7.4 and 0.1% Tween-20) per well. The samples were incubated for 1 h at room temperature (RT) with gentle shaking after which the plate was washed four times with a buffer containing 40 mM Tris-HCl (pH 8.8), 1 mM EDTA, 50 mM NaCl, 0.1% Tween-20) with an automatic microplate washer (Tecan 96 PW). The bound PCR products were denatured with 100 µl of 50 mM NaOH for 5 min at RT. The wells were then washed four times with the washing buffer.

The minisequencing reaction mixture, containing the detection step primer (5'-GTA GAC CTT GGT GTA GAC TC-3' (SEQ ID NO: 6)) at 0.2 µM concentration, the appropriate $^3$H dNTPs (dCTP for the amplification products deriving from the reference DNA templates and dGTP for the amplification product deriving from the sequence modified cDNA) (Amersham Biosciences) at 0.02 µM concentration and 0.5 U of Dynazyme DNA polymerase in 100 µl of 1×PCR buffer were added to wells. The wells were incubated at 55° C. for 15 min with gentle shaking. The wells were washed four times with the washing buffer and the incorporated radioactivity was measured in a beta counter MicroBeta (EG&G Wallac) and expressed as counts per minute (CPM). Amplification products deriving from the controls were minisequenced with four different $^3$H dNTPs (dGTP, dCTP, dATP, and dTTP). The minisequencing analysis for each sample was performed in two parallel reactions for each of the nucleotides.

Results

Figure 3:
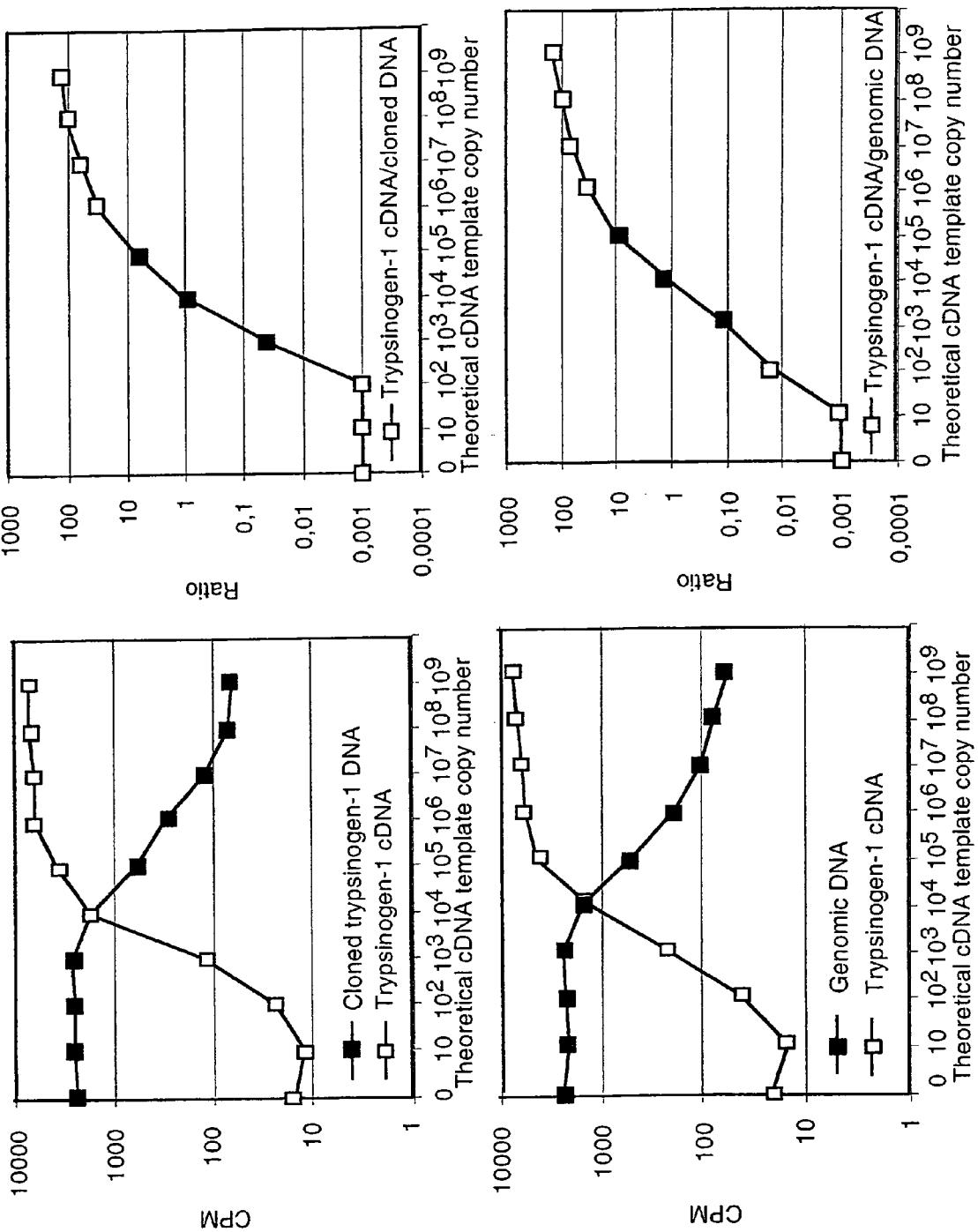

To determine the measuring range of the assay, 10-fold dilutions of the cDNA transcribed from $10^9$ copies of trypsinogen-1 cRNA and the reference DNA template ($10^3$ copies of cloned trypsinogen-1 DNA or genomic DNA from 500 cells) were co-amplified. All nested PCR amplification reactions were run to the plateau phase. The measuring range of the assay was more than two orders of magnitude, ranging from a theoretical cDNA to DNA ratio of less than 1:1 ($10^3$ copies of cDNA and $10^3$ copies of cloned DNA or genomic DNA from 500 cells) to over 100:1 ($10^5$ copies of cDNA and $10^3$ copies of cloned DNA or genomic DNA from 500 cells). The theoretical cDNA template copy number is based on the assumption that the efficiency of the reverse transcription reaction was 100%. (FIG. 3).

Figure 4:
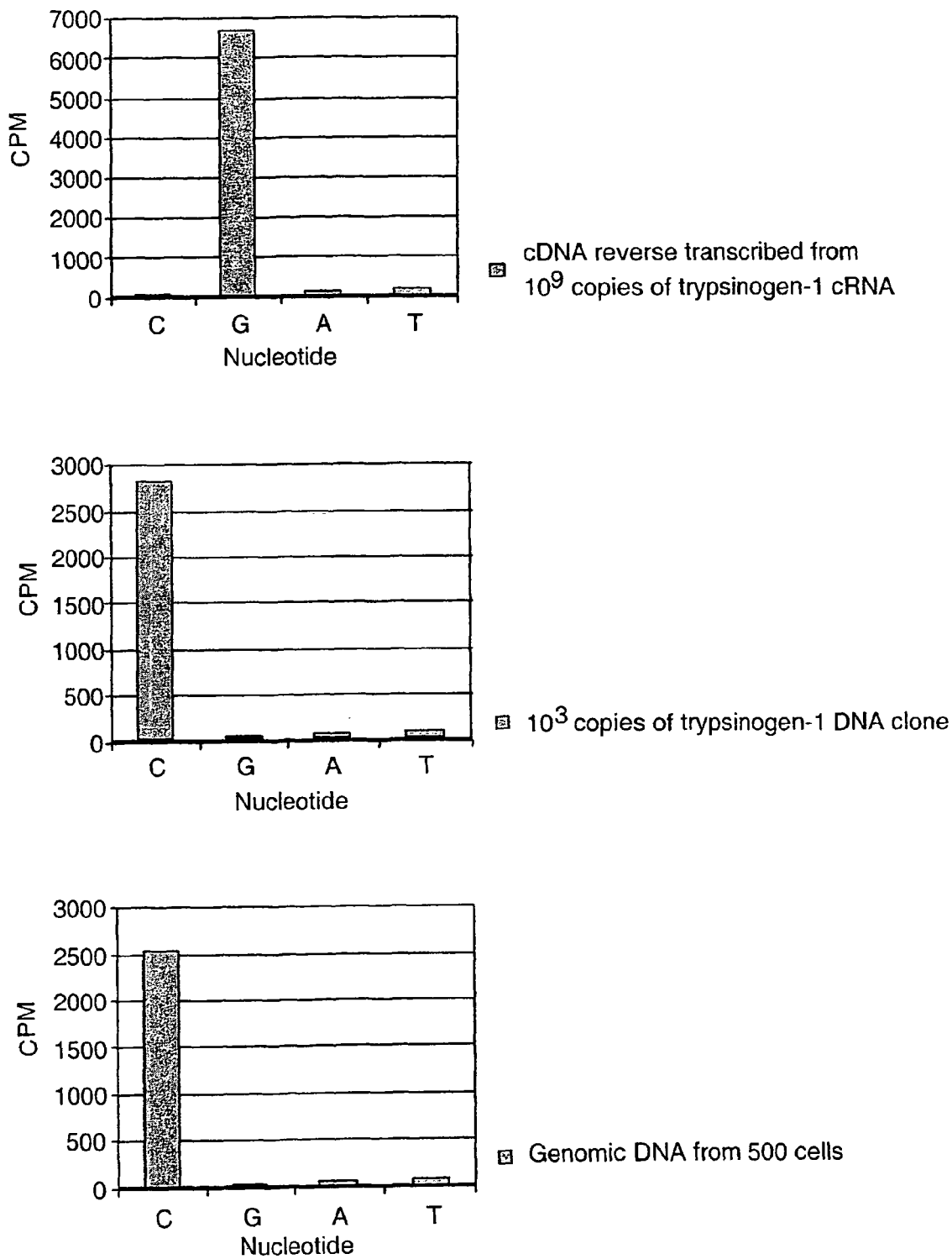

The minisequencing assay provided accurate discrimination of single nucleotide sequence differences in the separately amplified trypsinogen-1 cDNA, cloned trypsinogen-1 DNA, and genomic DNA products. The amplification product of trypsinogen-1 cDNA was detected with $^3$H-labelled dGTP while those of cloned trypsinogen-1 DNA and genomic DNA were detected with $^3$H-labelled dCTP. Mispriming of the minisequencing detection primers was excluded by minisequencing all the amplification products with $^3$H-labelled dATP and dTTP. (FIG. 4).

EXAMPLE 2

Experimental Design and Proving the Principle

The experiment was conducted in order to test the reproducibility of the assay in analyzing a gene expression profile in a cell line. In this experiment the expression profiles of five genes (matrix-metalloproteinase-2 (MMP-2), matrix-metalloproteinase-9 (MMP-9), urokinase-type plasminogen activator (uPA), urokinase-type plasminogen activator receptor (uPAR) and p53) in COLO 205 human colon adenocarcinoma cells was analyzed by first conducting a multiplexed reverse transcription step of mRNA extracted from the COLO 205 cells with sequence-modifying primers for each of the five genes. This was followed by individual gene-specific amplification reactions, so that in each of the reactions sequence-modified cDNA and genomic DNA, which served as reference DNA template, were co-amplified in a competitive manner, using the same gene-specific primers. The amplification products of the sequence modified cDNA and genomic DNA templates were detected and quantified by cyclic minisequencing (Järveläinen et al., Hepatology (2001), 33:1148-1153). The gene-specific cDNA over DNA ratios determined in the individual amplification reactions were combined to generate a profile of said ratios that reflected the relative amounts of mRNA transcripts originally present in the sample.

Preparative Steps

COLO 205 cells (American Type Culture Collection, Rockville, Md., USA) were grown at 37° C. in a humidified atmosphere with 5% $CO_2$. The cells were maintained in RPMI 1640 medium supplemented with 10% heat-inactivated fetal bovine serum, 2 mM L-glutamine and 100 units/ml penicillin and 100 µg/ml streptomycin. For each of the experiments, the same mRNA sample extracted from COLO 205 using Oligotex Direct mRNA Kit (Qiagen) was used. Human genomic DNA was purchased from Roche Diagnostic (Mannheim, Germany).

The Analytical Procedure

Reverse Transcription

Reverse transcription was performed using SuperScript II Reverse Transcriptase (Invitrogen) according to the manufacturer's instructions by first combining in a 12-µl reaction volume 2 pmol of each of the sequence-modifying antisense primers to create a single nucleotide A to G substitution (underlined) in the generated cDNA (5'-GGG AAT GGT TGA AGG GAG GGG C<u>G</u>G GGA G-3' (SEQ ID NO: 7) (MMP-2), 5'-AAA GGT TAG AGA ATC CAA GTT T<u>G</u>T TAG A-3' (SEQ ID NO: 8) (MMP-9), 5'-ATT CAG TGT AAG GAG TGG TCC TC<u>G</u> CCC CA-3' (SEQ ID NO: 9) (uPA), 5'-CAA CAC AAC AGC GGC AAC AAT ATT <u>G</u>AT AAT (SEQ ID NO: 10) (uPAR), and 5'-AAG GGT GGG GTG AAA ATG C<u>G</u>G ATG T-3' (SEQ ID NO: 11) (p53)), 0.5 mM dNTP, and mRNA extracted from $10^5$ COLO 205 cells and incubating at 65° C. for 5 min. After this the RT reaction was continued in a 20-µl reaction volume in first-strand buffer (50 mM Tris acetate, pH 8.3; 75 mM potassium acetate; 3 mM magnesium chloride) containing 10 mM DTT and 200 U of SuperScript RT at 42° C. for 50 min after which the reaction was inactivated by heating at 70° C. for 15 min.

Exonuclease I Treatment

Following reverse transcription, the unbound sequence-modifying reverse transcription primers were degraded by exonuclease I (New England Biolabs) in a 25-µl reaction volume in 1× restriction buffer (67 mM Glycine-KOH, 6.7 mM MgCl$_2$, 10 mM 2-mercaptoethanol, pH 9.5) and with 20 U of exonuclease I at 37° C. for 60 min and at 80° C. for 20 min.

Polymerase Chain Reaction 2.5 µl of the reverse transcription product was co-amplified with 2 ng of human genomic DNA in separate gene-specific amplification reactions in a 25-µl reaction volume in 1×PCR buffer (10mM tris-HCl, pH 8.8, 1.5 mM MgCl$_2$, 50 mM KCl, 0.1% Triton X-100; Finnzymes), containing 0.2 mM of each dNTP, 20 pmol of the sense primer (5'-CTG GAT GGA GGA AAA CCA AG-3' (SEQ ID NO: 12) (MMP-2), 5'-TGG GCC CTC TCT TCT CA-3' (SEQ ID NO: 13) (MMP-9), 5'-TTG GCC AGT TAT CCC TTC-3' (SEQ ID NO: 14) (uPA), 5'-GAA GAG AAA AGC TGG AGG AAG G-3' (SEQ ID NO: 15) (uPAR), or 5'-TGG AGC TGG AAG GGT CAA-3' (SEQ ID NO: 16) (p53)), 20 pmol of the antisense primer (5'-GGG AAT GGT TGA AGG GAG-3' (SEQ ID NO: 17) (MMP-2), 5'-AAA GGT TAG AGA ATC CAA GTT-3' (SEQ ID NO: 18) (MMP-9), 5'-ATT CAG TGT AAG GAG TGG TC-3' (SEQ ID NO: 19) (uPA), 5'-CAA CAC AAC AGC GGC AAC AA-3' (SEQ ID NO: 20) (uPAR), or 5'-AAG GGT GGG GTG AAA ATG-3' (SEQ ID NO: 21) (p53)), and 2 U of Dynazyme II DNA polymerase (Finnzymes) by first denaturing the templates for 5 min at 95° C. and then amplifying them for 35 cycles at 95° C. for 1 min and at 55° C. for 1 min. Contamination of mRNA samples with cDNA was excluded by performing control reactions without reverse transcriptase for each of the samples. A 15-µl aliquot of the PCR product was separated in 2% agarose gel and stained with ethidium bromide in order to exclude non-specific amplification.

Quantitative Detection by Cyclic Minisequencing

The amplification products of the sequence modified cDNA and genomic DNA templates were detected by cyclic minisequencing described by Järveläinen et al. (Hepatology, 2001, 33:1148-1153), a modification of solid-phase minisequencing using $^3$H-labeled nucleotides (Syvänen et al., Genomics (1990), 8:684-692; Ihalainen et al., Biotechniques (1994), 16:938-943; Suomalainen and Syvänen, Methods Mol. Biol. (1998), 86:121-131) with minor modifications. Following PCR amplification, the unreacted dNTPs and primers were removed by adding 1 U of shrimp alkaline phosphatase (Roche) and 5 U of exonuclease I directly to the PCR reaction. The degradation of primers and dNTPs was performed at 37° C. for 30 min, after which the enzymes were inactivated by incubation at 80° C. for 15 min. The enzyme-treated PCR products were then filtered together with 220 µl of water using Microcon-96 YM filtrate assembly with YM-30 filter units (50 bp cut-off for double-stranded DNA) and then washed twice with 250 µl of water. Finally, the retentates were recovered by centrifuging and the volumes were adjusted to 50 µl. Four aliquots, 5 µl each, of the filtered PCR products were transferred to 96-well PCR plates (Thermo-Fast 96, Abgene, Epsom, Surrey, England) containing reagents for the cyclic minisequencing reaction. These wells contained 3 pmol of the biotinylated cyclic minisequencing primer (5'Biotin-TTC CCG CTC AGC CCT CCC-3' (SEQ ID NO: 22) (MMP-2), 5'Biotin-TTG TTT TTT GTT GGA GTG TTT CTA A-3' (SEQ ID NO: 23) (MMP-9), 5'Biotin-CCA ATC CTC ACT GGG TGG GG-3' (SEQ ID NO: 24) (uPA), 5'Biotin-ATG GGA GAG CTC TTG TTA TTA T-3' (SEQ ID NO: 25) (uPAR), or 5'Biotin-TTT TAC ATT CTG CAA GCA CAT C-3' (SEQ ID NO: 26) (p53)), 2 pmol of the $^3$H-labeled nucleotides, dCTP or dTTP, and 0.5 U of Dynazyme DNA polymerase in 15 µl of Dynazyme buffer.

The plate was covered with the aluminium sealing tape (Adhesive PCR Foil Seal, Abgene), and the cyclic primer extension was performed by cycling at 96° C. for 10 s and at 57° C. for 10 s, for 50 cycles. After cycling, the whole cyclic minisequencing reactions were transferred to streptavidin-coated scintillating microtitration plate wells (Perkin-Elmer Wallac) with 20 µl of buffer (0.15 M NaCl, 20 mM Na-phosphate pH 7.4 and 0.1% Tween-20) per well. The samples were incubated for 1 h at room temperature (RT) with gentle shaking after which the plate was washed once with TENT buffer (40 mM Tris-HCl (pH 8.8), 1 mM EDTA, 50 mM NaCl, 0.1% Tween-20) with an automatic microplate washer (Tecan 96 PW), once with 50 mM NaOH for 5 min at RT, and once again with TENT buffer. The incorporated radioactivity was measured in a beta counter MicroBeta (EG&G Wallac) and expressed as counts per minute (CPM). The minisequencing analysis for each sample was performed in two parallel reactions for each of the labeled nucleotides.

Results

Figure 5:
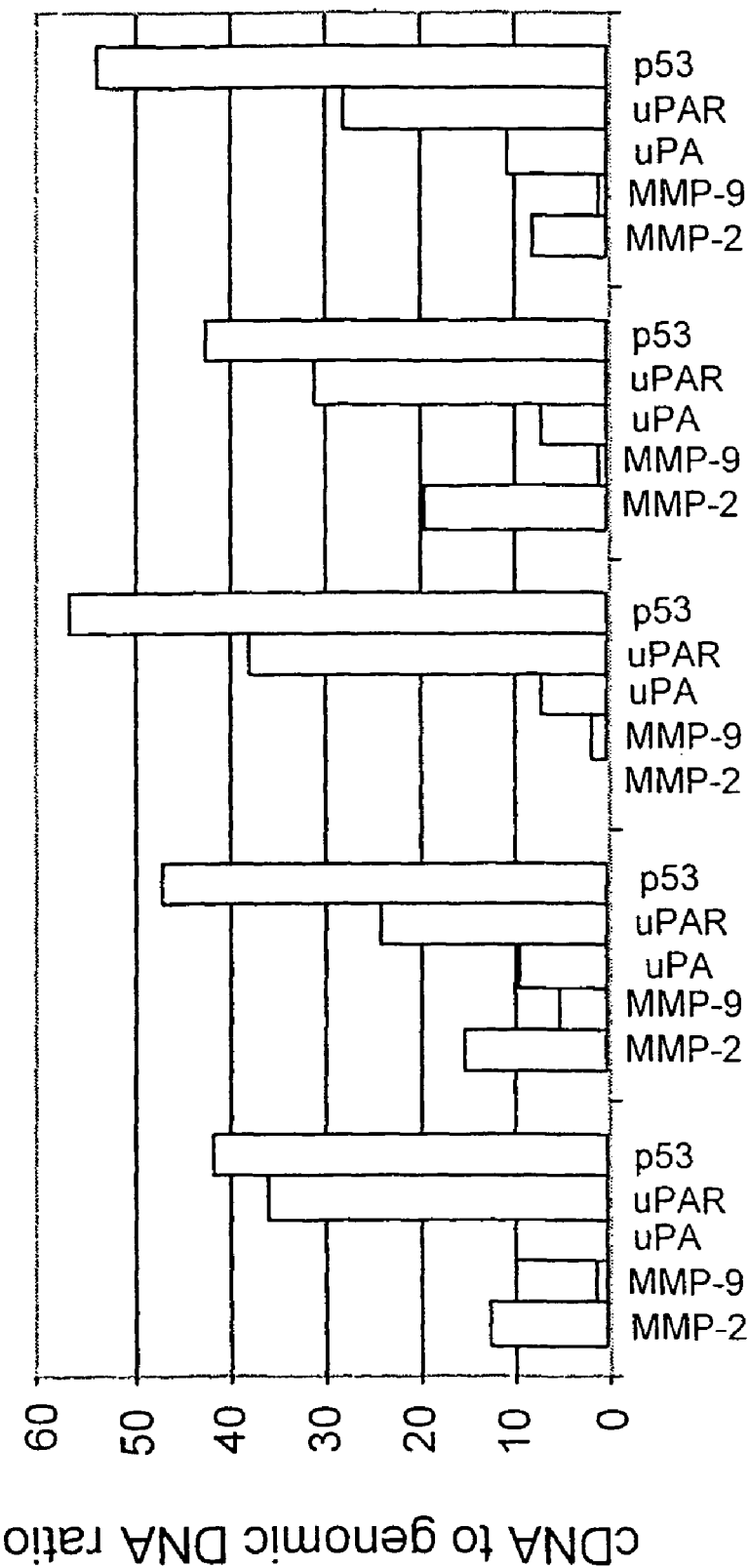
Figure 6:
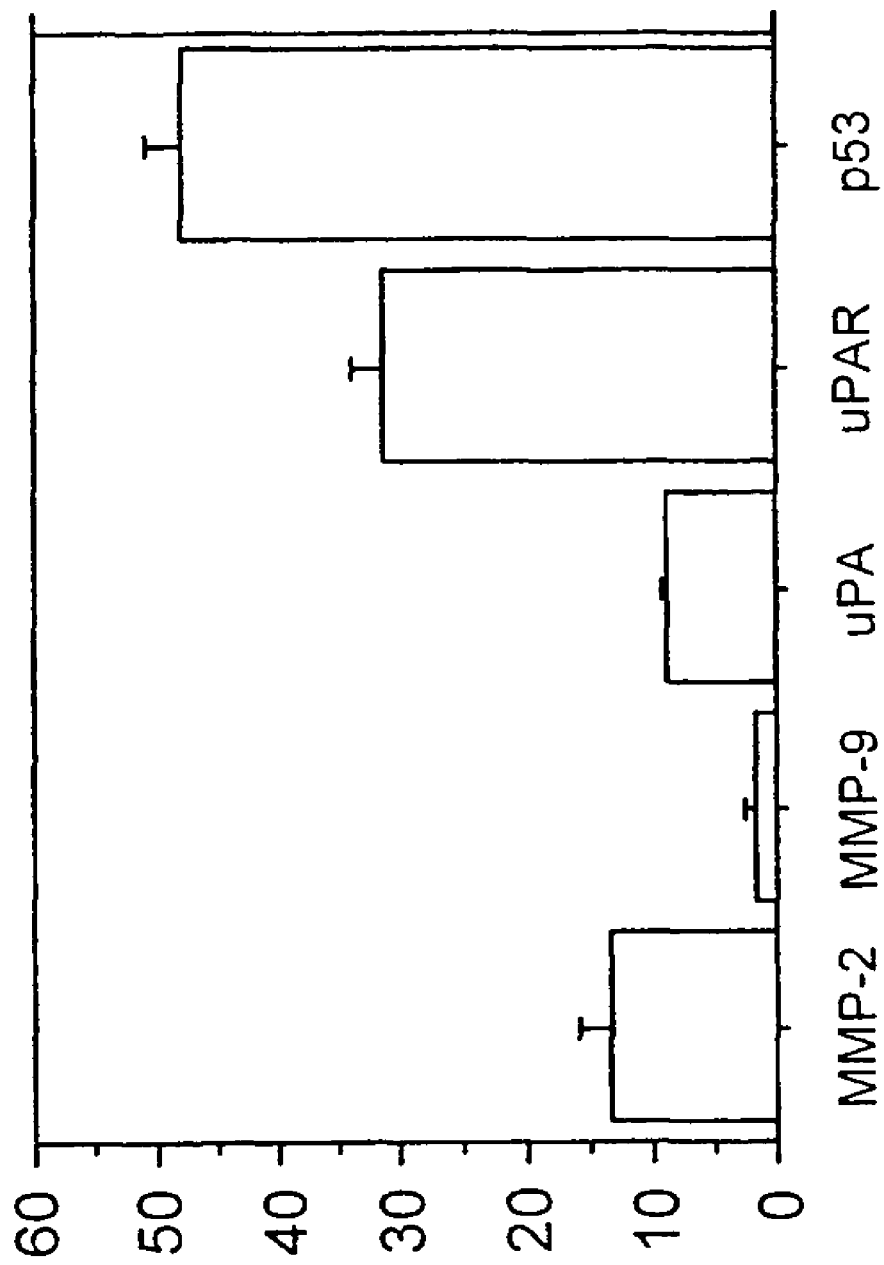

The assay is reproducible as shown in FIGS. 5 and 6. The mean values and standard errors were 13.5 and 2.4, respectively, for MMP-2, 1.7 and 0.8 for MMP-9, 8.5 and 0.7 for uPA, 31.2 and 2.5 for uPAR, and 48.1 and 2.9 for p53 (FIG. 6).

EXAMPLE 3

Experimental Design and Proving the Principle

The experiment was conducted in order to define the measuring range of the assay over a range of cDNA/DNA ratios. In this experiment the principle of the present invention was proven by analyzing a dilution series of sequence-modified cDNA reverse-transcribed from the cRNA of a single gene in relation to the reference DNA template which was 20 ng of human genomic DNA corresponding to about $10^4$ copies of each gene. PCR was performed on a LightCycler instrument (Roche Applied Science) and the amplification products of the sequence modified cDNA and genomic DNA templates were detected and quantified by melting curve analysis on the LightCycler instrument.

Preparative Steps

Full-length trypsinogen-2 and MMP-2 cDNA clones were obtained from American Type Culture Collection. The sequences of the cDNA clones were checked by sequencing from both ends on an ABI Prism 310 genetic analyzer, (Applied Biosystems) using the ABI Prism dye terminator cycle sequencing core kit and AmpliTaq DNA polymerase. Trypsinogen-2 and MMP-2 cRNAs were generated by in vitro transcription using trypsinogen-2 and MMP-2 cDNA clones as templates (Epicentre Technologies), and purified by RNeasy Mini Kit (Qiagen).

The Analytical Procedure

Reverse Transcription

Reverse transcription was performed using DyNAmo Capillary SYBR Green 2-step qRT-PCR Kit (Finnzymes) according to the manufacturer's instructions using the sequence-modifying antisense primers to create five (trypsinogen-2) or six (MMP-2) nucleotide A to G or T to C substitutions (underlined) in the generated cDNA (5'-CCA CAC AGA ACA TGT TGC TGG CGG CCC TTC CA-3' (SEQ ID NO: 27) (trypsinogen-2) and 5'-GAA GAG ACT CGG TAG GGA CAC GC CGGGG CGG AGT GA-3' (SEQ ID NO: 28) (MMP-2)) using $5 \times 10^9$ copies of trypsinogen-2 or MMP-2 cRNA as templates.

Exonuclease I Treatment

Following reverse transcription, the unbound sequence-modifying reverse transcription primers were degraded by exonuclease I (New England Biolabs) in a 25-µl reaction volume in 1× restriction buffer (67 mM Glycine-KOH, 6.7 mM $MgCl_2$, 10 mM 2-mercaptoethanol, pH 9.5) and with 20 U of exonuclease I at 37° C. for 60 min and at 80° C. for 20 min. The exonuclease I treated cDNA was serially diluted 10-fold prior to amplification.

Polymerase Chain Reaction 2.5 µl of each of the dilutions of the exonuclease I treated reverse transcription products were amplified with 20 ng of human genomic DNA in gene-specific amplification reactions using DyNAmo Capillary SYBR Green 2-step qRT-PCR Kit (Finnzymes) according to the manufacturer's instructions using primers 5'-GCC AGG CTA AGT GTG AAG-3' (SEQ ID NO: 29) (trypsinogen-2 sense), 5'-CCA CAC AGA ACA TGT TGC T-3' (SEQ ID NO: 30) (trypsinogen-2 antisense), 5'-CTG GAT GGA GGA AAA CCA AG-3' (SEQ ID NO: 31) (MMP-2sense), 5'-GGG AAT GGT TGA AGG GAG-3' (SEQ ID NO: 32) (MMP-2 antisense) for 30 cycles. PCR was performed in a LightCycler instrument (Roche Applied Science) for 30 cycles with denaturation at 95° C. (15 s hold) and annealing at 57° C. (1 min hold). The temperature transition rate was 20° C./s, and fluorescense was acquired at the end of annealing. Contamination of cRNA samples with cDNA was excluded by performing control reactions without reverse transcriptase for each of the samples. A 15-µl aliquot of the PCR product was separated in 2% agarose gel and stained with ethidium bromide in order to exclude non-specific amplification.

Melting Curve Acquisition and Analysis

The amplification products of the sequence modified cDNA and genomic DNA templates were detected and quantified by melting curve analysis on the LightCycler instrument immediately following amplification with an additional denaturation at 95° C. with a 0 s hold, cooling at a rate of 20° C./s to 57° C., and a continuous melting curve acquisition during a 0.1° C./s ramp to 98° C. A derivative melting curve plot was obtained with the use of default settings of the LightCycler software.

Results

Figure 7:
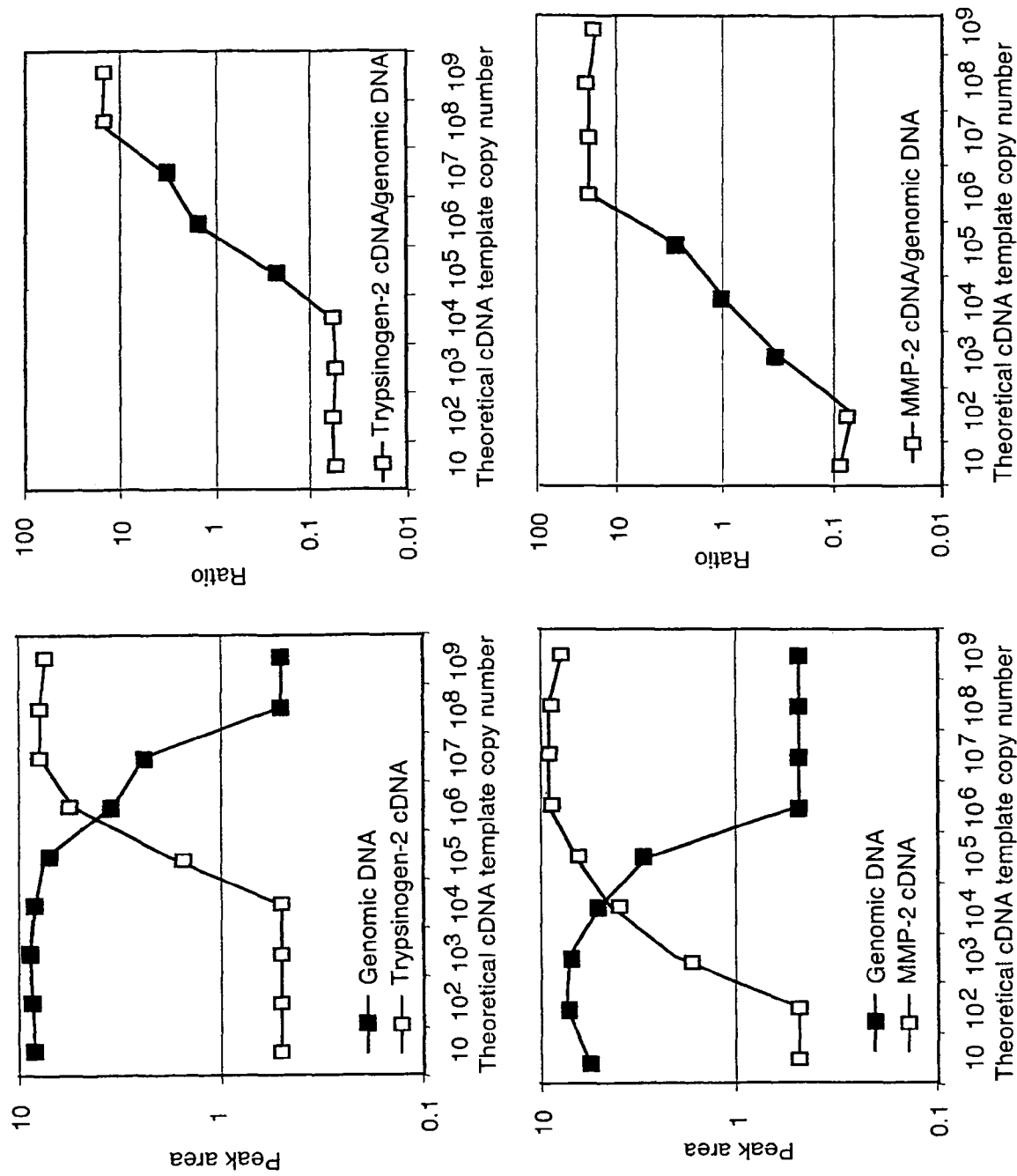

By using the sequence-modifying primers to create five or six nucleotide A to G or T to C substitutions in the generated cDNAs, we were able to detect and quantify the amplification products of the cDNAs and genomic DNA, differing in their melting temperatures by approximately 4° C., using melting curve analysis. To determine the measuring range of the assay, 10-fold dilutions of the cDNA transcribed from $10^9$ copies of trypsinogen-2 cRNA or MMP-2 cRNA were co-amplified with 20 ng of human genomic DNA. The measuring range of the assay for trypsinogen-2 was more than two orders of magnitude, ranging from a theoretical cDNA to DNA ratio of less than 10:1 ($10^5$ copies of cDNA and 20 ng of human genomic DNA corresponding to about $10^4$ copies of the gene) to over 1000:1 ($10^7$ copies of cDNA and 20 ng of human genomic DNA corresponding to about $10^4$ copies of the gene). The measuring range of the assay for MMP-2 was more than two orders of magnitude, ranging from a theoretical cDNA to DNA ratio of less than 1:10 ($10^3$ copies of cDNA and 20 ng of human genomic DNA corresponding to about $10^4$ copies of the gene) to over 10:1 ($10^5$ copies of cDNA and 20 ng of human genomic DNA corresponding to about $10^4$ copies of the gene). The theoretical cDNA template copy number is based on the assumption that the efficiency of the reverse transcription reaction was 100%. (FIG. 7).

The invention claimed is:

1. A method for quantitative and/or comparative assessment of the relative amounts of mRNA transcripts present in a cell or tissue sample, the method comprising the steps of:
   a) carrying out reverse transcription of the mRNA contained in the sample using sequence-modifying primers for several genes in the same reaction to obtain a pool of sequence-modified cDNA molecules, wherein the sequence-modifying primers are oligonucleotides comprising three functional segments:
      i. a 5'-terminal segment comprising a nucleotide sequence, which is complementary to the mRNA sequence as well as the sense strand DNA sequence of a specific gene and contains the complementary nucleotide sequence of the binding sites for the downstream primers used in subsequent amplification reactions,
      ii. a central segment consisting of a nucleotide sequence comprising one or multiple nucleotides, which are non-complementary to the mRNA sequence as well as the sense strand DNA sequence of said gene, and
      iii. a 3'-terminal segment comprising a nucleotide sequence, which is complementary to the mRNA sequence as well as the sense strand DNA sequence of said gene,
   b) removing or inactivating redundant sequence-modifying primers after completion of the reverse transcription,
   c) carrying out individual amplification reactions for each of the analyzed genes, so that in each of the reactions sequence-modified cDNA templates are co-amplified with a reference DNA template, using gene-specific primers to generate measurable amounts of amplification products, wherein the gene-specific primers have binding sites which are located on the same exon,
   d) quantitatively measuring the amounts and determining the relative levels of the amplification products derived from sequence-modified cDNA and reference DNA templates to obtain a gene-specific cDNA over DNA ratio in each of the individual amplification reactions, and
   e) combining the gene-specific cDNA over DNA ratios determined in the individual amplification reactions to generate a sample-specific profile of said ratios that reflects the relative amounts of mRNA transcripts originally present in the sample.

2. The method according to claim 1, wherein the sample comprises a cell or tissue lysate or homogenate.

3. The method according to claim 1, wherein RNA or RNA and DNA is isolated from the sample prior to reverse transcription.

4. The method according to claim 1, wherein the reverse transcription reaction is carried out under conditions where DNA contained in the sample remains double-stranded.

5. The method according to claim 1, wherein removing or inactivating redundant sequence-modifying primers after completion of the reverse transcription is carried out by enzymatic degradation.

6. The method according to claim 5, wherein said enzymatic degradation is carried out using single-stranded DNA-specific exonuclease.

7. The method according to claim 1, wherein the individual amplification reactions are carried out in physically separate reaction vessels.

8. The method according to claim 1, wherein the reference DNA template comprises genomic DNA contained in the sample or isolated from a separate source.

9. The method according to claim 1, wherein the reference DNA template comprises cloned or synthesized DNA oligo- or polynucleotides.

10. The method according to claim 1, wherein the cDNA and reference DNA templates in an individual amplification reaction are co-amplified in a competitive manner, using the same primers.

11. The method according to claim 1, comprising modifying the nucleotide sequence of the cDNA molecules generated during reverse transcription and using these sequence modifications to distinguish the cDNA-derived amplification products from the reference DNA template-derived amplification products present in the same amplification reaction.

12. The method according to claim 1, wherein the quantitative measurement of the amplification products is carried out during amplification.

13. The method according to claim 1, wherein the quantitative measurement of the amplification products is carried out after completion of the amplification reaction.

14. The method according to claim 1, wherein the relative levels of amplification products deriving from sequence-modified cDNA and reference DNA templates in an individual gene-specific amplification reaction reflect the relative amounts of said templates originally present in the amplification reaction prior to amplification.

15. The method according to claim 1, wherein the amplification of the cDNA and reference DNA templates is carried out by a method selected from polymerase chain reaction, ligase chain reaction and transcription-mediated amplification.

16. The method according to claim 10, wherein the amplification of the cDNA and reference DNA templates is carried out by a method selected from polymerase chain reaction, ligase chain reaction and transcription-mediated amplification.

17. The method according to claim 1, wherein the quantitative measurement of the amplification products is carried out by a method selected from the group consisting of melting curve analysis, mass spectrometry, assays based on primer extension at the site of differentiation, assays based on sequence specific hybridization probes, and assays based on direct or indirect fluorescent resonance energy transfer.

18. The method according to claim 17, wherein the assays based on primer extension at the site of differentiation are selected from the group consisting of minisequencing, cyclic minisequencing, and assays based on allele-specific primer extension.

19. The method according to claim 17, wherein the sequence-specific hybridization probes are dual labeled hydrolysis probes.

20. The method according to claim 11, wherein the quantitative measurement of the amplification products is carried out by a method selected from the group consisting of melting curve analysis, mass spectrometry, assays based on primer extension at the site of differentiation, assays based on sequence specific hybridization probes, and assays based on direct or indirect fluorescent resonance energy transfer.

21. The method according to claim 20, wherein the assays based on primer extension at the site of differentiation are selected from the group consisting of minisequencing, cyclic minisequencing, and assays based on allele-specific primer extension.

22. The method according to claim 20, wherein the sequence-specific hybridization probes are dual labeled hydrolysis probes and probes.

23. The method according to claim 1, wherein the method applies a test kit that comprising sequence-modifying primers for several genes, a means for removing or inactivating redundant sequence-modifying primers after completion of the reverse transcription, and gene-specific primers suitable for co-amplification of sequence-modified cDNA templates and a reference DNA template in a competitive manner in individual amplification reactions for each of the analyzed genes.

24. The method according to claim 1, wherein the gene-specific primers generate cDNA and DNA derived amplification products of equal length.

* * * * *

SEQUENCE LISTING

<160> NUMBER OF SEQ ID NOS: 32

<210> SEQ ID NO 1
<211> LENGTH: 34
<212> TYPE: DNA
<213> ORGANISM: Artificial Sequence
<220> FEATURE:
<223> OTHER INFORMATION: chemically synthesized sequence-modifying
      antisense primer

<400> SEQUENCE: 1
cacatagttg tagaccttgg tgtagactcg aggc                                 34

<210> SEQ ID NO 2
<211> LENGTH: 18
<212> TYPE: DNA
<213> ORGANISM: Artificial Sequence
<220> FEATURE:
<223> OTHER INFORMATION: chemically synthesized sense primer

```
<400> SEQUENCE: 2
tgattctggt ggccctgt                                                      18

<210> SEQ ID NO 3
<211> LENGTH: 22
<212> TYPE: DNA
<213> ORGANISM: Artificial Sequence
<220> FEATURE:
<223> OTHER INFORMATION: chemically synthesized antisense primer

<400> SEQUENCE: 3
cacatagttg tagaccttgg tg                                                 22

<210> SEQ ID NO 4
<211> LENGTH: 18
<212> TYPE: DNA
<213> ORGANISM: Artificial Sequence
<220> FEATURE:
<223> OTHER INFORMATION: chemically synthesized nested sense primer

<400> SEQUENCE: 4
ctggtggccc tgtggtct                                                      18

<210> SEQ ID NO 5
<211> LENGTH: 18
<212> TYPE: DNA
<213> ORGANISM: Artificial Sequence
<220> FEATURE:
<223> OTHER INFORMATION: chemically synthesized nested antisense primer

<400> SEQUENCE: 5
agaccttggt gtagactc                                                      18

<210> SEQ ID NO 6
<211> LENGTH: 20
<212> TYPE: DNA
<213> ORGANISM: Artificial Sequence
<220> FEATURE:
<223> OTHER INFORMATION: chemically synthesized detection step primer

<400> SEQUENCE: 6
gtagaccttg gtgtagactc                                                    20

<210> SEQ ID NO 7
<211> LENGTH: 28
<212> TYPE: DNA
<213> ORGANISM: Artificial Sequence
<220> FEATURE:
<223> OTHER INFORMATION: chemically synthesized MMP-2 sequence-modifying
      antisense primer

<400> SEQUENCE: 7
gggaatggtt gaagggaggg gcggggag                                           28

<210> SEQ ID NO 8
<211> LENGTH: 28
<212> TYPE: DNA
<213> ORGANISM: Artificial Sequence
<220> FEATURE:
<223> OTHER INFORMATION: chemically synthesized MMP-9 sequence modifying
      antisense primer

<400> SEQUENCE: 8
aaaggttaga gaatccaagt ttgttaga                                           28
```

```
<210> SEQ ID NO 9
<211> LENGTH: 29
<212> TYPE: DNA
<213> ORGANISM: Artificial Sequence
<220> FEATURE:
<223> OTHER INFORMATION: chemically synthesized uPA sequence-mofifying
      antisense primer

<400> SEQUENCE: 9
attcagtgta aggagtggtc ctcgcccca                                    29

<210> SEQ ID NO 10
<211> LENGTH: 30
<212> TYPE: DNA
<213> ORGANISM: Artificial Sequence
<220> FEATURE:
<223> OTHER INFORMATION: chemically synthesized uPAR sequence-modifying
      antisense primer

<400> SEQUENCE: 10
caacacaaca gcggcaacaa tattgataat                                   30

<210> SEQ ID NO 11
<211> LENGTH: 25
<212> TYPE: DNA
<213> ORGANISM: Artificial Sequence
<220> FEATURE:
<223> OTHER INFORMATION: chemically synthesized p53 sequence-modifying
      antisense primer

<400> SEQUENCE: 11
aagggtgggg tgaaaatgcg gatgt                                        25

<210> SEQ ID NO 12
<211> LENGTH: 20
<212> TYPE: DNA
<213> ORGANISM: Artificial Sequence
<220> FEATURE:
<223> OTHER INFORMATION: chemically synthesized MMP-2 sense primer

<400> SEQUENCE: 12
ctggatggag gaaaaccaag                                              20

<210> SEQ ID NO 13
<211> LENGTH: 17
<212> TYPE: DNA
<213> ORGANISM: Artificial Sequence
<220> FEATURE:
<223> OTHER INFORMATION: chemically synthesized MMP-9 sense primer

<400> SEQUENCE: 13
tgggccctct cttctca                                                 17

<210> SEQ ID NO 14
<211> LENGTH: 18
<212> TYPE: DNA
<213> ORGANISM: Artificial Sequence
<220> FEATURE:
<223> OTHER INFORMATION: chemically synthesized uPA sense primer

<400> SEQUENCE: 14
ttggccagtt atcccttc                                                18

<210> SEQ ID NO 15
<211> LENGTH: 22
<212> TYPE: DNA
```

```
<213> ORGANISM: Artificial Sequence
<220> FEATURE:
<223> OTHER INFORMATION: chemically synthesized uPAR sense primer

<400> SEQUENCE: 15
gaagagaaaa gctggaggaa gg                                              22

<210> SEQ ID NO 16
<211> LENGTH: 18
<212> TYPE: DNA
<213> ORGANISM: Artificial Sequence
<220> FEATURE:
<223> OTHER INFORMATION: chemically synthesized p53 sense primer

<400> SEQUENCE: 16
tggagctgga agggtcaa                                                   18

<210> SEQ ID NO 17
<211> LENGTH: 18
<212> TYPE: DNA
<213> ORGANISM: Artificial Sequence
<220> FEATURE:
<223> OTHER INFORMATION: chemically synthesized MMP-2 antisense primer

<400> SEQUENCE: 17
gggaatggtt gaagggag                                                   18

<210> SEQ ID NO 18
<211> LENGTH: 21
<212> TYPE: DNA
<213> ORGANISM: Artificial Sequence
<220> FEATURE:
<223> OTHER INFORMATION: chemically synthesized MMP-9 antisense primer

<400> SEQUENCE: 18
aaaggttaga gaatccaagt t                                               21

<210> SEQ ID NO 19
<211> LENGTH: 20
<212> TYPE: DNA
<213> ORGANISM: Artificial Sequence
<220> FEATURE:
<223> OTHER INFORMATION: chemically synthesized uPA antisense primer

<400> SEQUENCE: 19
attcagtgta aggagtggtc                                                 20

<210> SEQ ID NO 20
<211> LENGTH: 20
<212> TYPE: DNA
<213> ORGANISM: Artificial Sequence
<220> FEATURE:
<223> OTHER INFORMATION: chemically synthesized uPAR antisense primer

<400> SEQUENCE: 20
caacacaaca gcggcaacaa                                                 20

<210> SEQ ID NO 21
<211> LENGTH: 18
<212> TYPE: DNA
<213> ORGANISM: Artificial Sequence
<220> FEATURE:
<223> OTHER INFORMATION: chemically synthesized p53 antisense primer

<400> SEQUENCE: 21
aagggtgggg tgaaaatg                                                   18
```

```
<210> SEQ ID NO 22
<211> LENGTH: 18
<212> TYPE: DNA
<213> ORGANISM: Artificial Sequence
<220> FEATURE:
<223> OTHER INFORMATION: chemically synthesized MMP-2 biotinylated
      cyclic minisequencing primer

<400> SEQUENCE: 22
ttcccgctca gccctccc                                                  18

<210> SEQ ID NO 23
<211> LENGTH: 25
<212> TYPE: DNA
<213> ORGANISM: Artificial Sequence
<220> FEATURE:
<223> OTHER INFORMATION: chemically synthesized MMP-9 biotinylated
      cyclic minisequencing primer

<400> SEQUENCE: 23 ttgtttttg ttggagtgtt tctaa                                           25

<210> SEQ ID NO 24
<211> LENGTH: 20
<212> TYPE: DNA
<213> ORGANISM: Artificial Sequence
<220> FEATURE:
<223> OTHER INFORMATION: chemically synthesized uPA biotinylated cyclic
      minisequencing primer

<400> SEQUENCE: 24
ccaatcctca ctgggtgggg                                                20

<210> SEQ ID NO 25
<211> LENGTH: 22
<212> TYPE: DNA
<213> ORGANISM: Artificial Sequence
<220> FEATURE:
<223> OTHER INFORMATION: chemically synthesized uPAR biotinylated cyclic
      minisequencing primer

<400> SEQUENCE: 25
atgggagagc tcttgttatt at                                             22

<210> SEQ ID NO 26
<211> LENGTH: 22
<212> TYPE: DNA
<213> ORGANISM: Artificial Sequence
<220> FEATURE:
<223> OTHER INFORMATION: chemically synthesized p53 biotinylated cyclic
      minisequencing primer

<400> SEQUENCE: 26
ttttacattc tgcaagcaca tc                                             22

<210> SEQ ID NO 27
<211> LENGTH: 32
<212> TYPE: DNA
<213> ORGANISM: Artificial Sequence
<220> FEATURE:
<223> OTHER INFORMATION: chemically synthesized trypsinogen-2 sequence-
      modifying antisense primer

<400> SEQUENCE: 27
ccacacagaa catgttgctg gcggcccttc ca                                  32
```

```
<210> SEQ ID NO 28
<211> LENGTH: 35
<212> TYPE: DNA
<213> ORGANISM: Artificial Sequence
<220> FEATURE:
<223> OTHER INFORMATION: chemically synthesized MMP-2 sequence-modifying
      antisense primer

<400> SEQUENCE: 28
gaagagactc ggtagggaca cgccgggcgg agtga                              35

<210> SEQ ID NO 29
<211> LENGTH: 18
<212> TYPE: DNA
<213> ORGANISM: Artificial Sequence
<220> FEATURE:
<223> OTHER INFORMATION: chemically synthesized trypsinogen-2 sense
      primer

<400> SEQUENCE: 29
gccaggctaa gtgtgaag                                                 18

<210> SEQ ID NO 30
<211> LENGTH: 19
<212> TYPE: DNA
<213> ORGANISM: Artificial Sequence
<220> FEATURE:
<223> OTHER INFORMATION: chemically synthesized trypsinogen-2-antisense
      primer

<400> SEQUENCE: 30
ccacacagaa catgttgct                                                19

<210> SEQ ID NO 31
<211> LENGTH: 20
<212> TYPE: DNA
<213> ORGANISM: Artificial Sequence
<220> FEATURE:
<223> OTHER INFORMATION: chemically synthesized MMP-2 sense primer

<400> SEQUENCE: 31
ctggatggag gaaaaccaag                                               20

<210> SEQ ID NO 32
<211> LENGTH: 18
<212> TYPE: DNA
<213> ORGANISM: Artificial Sequence
<220> FEATURE:
<223> OTHER INFORMATION: chemically synthesized MMP-2 antisense primer

<400> SEQUENCE: 32
gggaatggtt gaagggag                                                 18
```